United States Patent [19]

van der Jagt

[11] Patent Number: Plant 5,878

[45] Date of Patent: Feb. 10, 1987

[54] CHRYSANTHEMUM NAMED 'ORANGE REFLA'

[75] Inventor: Martinus van der Jagt, Ter Aar, Netherlands

[73] Assignee: Chrysanthemum Breeders Association, N.V., Netherlands Antilles

[21] Appl. No.: 664,874

[22] Filed: Oct. 25, 1984

[51] Int. Cl.[4] ..... A01H 5/00

[52] U.S. Cl. ..... Plts./74

[58] Field of Search ..... Plt./74

*Primary Examiner*—James R. Feyrer

*Attorney, Agent, or Firm*—Parkhurst & Oliff

[57] ABSTRACT

A new and distinct cultivar of Chrysanthemum plant named 'Orange Refla', bearing large sized orange blooms with a green yellow center and a performance of seventeen days.

3 Drawing Figures

BACKGROUND OF THE NEW PLANT

The new plant of the present invention relates to the Cyrysanthemum genus.

BACKGROUND OF THE NEW PLANT

The new plant according to the present invention comprises a new and distinct cultivar of Chrysanthemum plane which is a color-mutant of Chrysanthemum names 'Pink Refla'. The new cultivar was discovered by Martinus van der Jagt in June, 1983 at Paradijsewg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a large sized bloom and orange color.

BRIEF DESCRIPTION OF THE DRAWINGS

The present new and distinct chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage and petiole of the new cultivar.

DESCRIPTION OF THE NEW PLANT

This new variety of Chrysanthemum is of the botanical classification *Chrysanthemum morifolium,* named 'Orange Refla'. When grown in the vicinity of Ter Aar, Holland, it has a response time of approximately eight and one-half weeks. This new variety produces large sized orange blooms with a green yellow center and having a performance of seventeen days. This new variety of Chrysanthemum has been found to retain its distinctive characteristics throughout successive propagations and may be planted under conventional greenhouse conditions in Holland between weeks 01–34.

The following is a description of the plant and characteristics that distinguish it over related known varieties and its antecedents:

Botanical classification: *Chrysanthemum morifolium.*

Bud:
- *Size.*—Medium.
- *Form.*—Flat top.
- *Outside Color.*—Saffron Yellow RHS 7/3.

Bloom:
- *Size.*—Large.
- Fully expanded.—7.5–9.5 cm. (approx.).
- *Borne.*—Single.
- *Stems.*—Strong.
- *Forms.*—Semi-double.
- *Permanence.*—17 days.

Color:
- *Center of flower (Disk Floret).*—Parsley Green RHS 00962/1+ Cadmium Orange RHS 8/2 Cross-section 1.5 cm. (approx).
- *Base of petals.*—Persimmon Orange RS 710/3.
- *Inside of petals.*—Persimmon Orange RHS 710/3.
- *Reverse of petals.*—Apricot RHS 609/2.
- *Outer petals.*—Persimmon Orange RHS 710/3.
- *Tonality from a distance.*—Large attractive orange flower with upstanding petals.
- *Discoloration.*—Small. To pale majolice yellow.

Petals:
- *Texture (Upper and underside).*—Rough.
- *Number.*—33–40.
- *Cross-section.*—Flat.
- *Arrangement.*—Imbricated.
- *Persistence.*—Petals rather strong. A little bit reflexion at edge when over-bloomed.
- *Fragrance.*—Chrysanthemum.

Reproductive organs:
- *Stamen.*—Normal for single.
- *Pollen.*—A few appear when blooming.
- *Styles.*—Green Yellow; Columnar, Length 5 mm. (approx.).
- *Length.*—Medium.
- *Stigmas.*—Normal Yellow; width 1.5 mm. (approx.).
- *Ovaries.*—Enclosed in calyx.

Plant:
- *Form.*—Herbaceous.
- *Growth.*—Very vigorous.
- *Height.*—115–120 cm.
- *Peduncle.*—Strong and tall. Near the top — 8 cm. (approx.). Near the bottom — 15 cm. (approx.). Near the bottom — 18 cm. (approx.).
- *Internodes.*—3.5–4 cm. (approx.).

*Flowering Response.*—8.5 to 9 weeks.

Foliage:

*Color.*—Normal green.

*Size.*—Length 12.5 cm. and width 7.5 cm. (approx.).

*Quantity.*—Normal to less.

*Shape.*—Pointed.

*Texture.*—Underside: Rough. Underside: Smooth.

*Ribs and Veins.—Upperside: Green. Underside: The main rib "lays on" the leaf.*

*Edge.*—Deep undulated.

*Leaf Underside:*—Smooth to heavy.

In the description above, color references are made to the "Horticultural Color Chart I & II" issued by the British Colour Council in collaboration with The Royal Horticultural Society, Copyright Robert F. Wilson, Vol I, 1938; Vol II, 1941, printed by Henry Stone & Son, Ltd., Banbury, England.

What is claimed is:

1. A new and distinct cultivar of Chrysanthemum named 'Orange Refla', as described and illustrated in the foregoing specification and accompanying drawings.

* * * * *

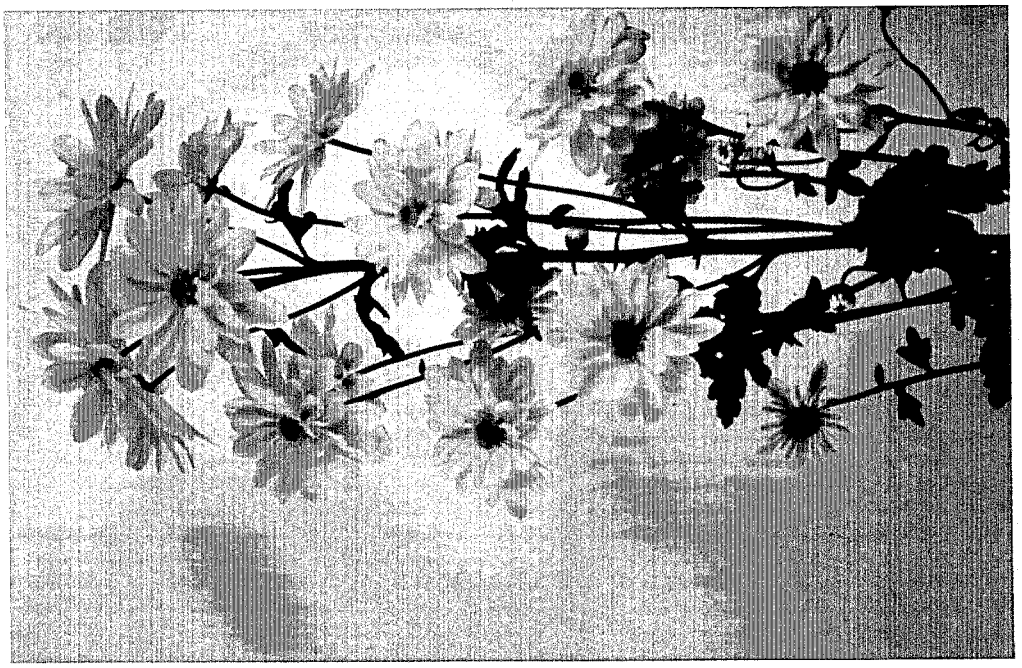
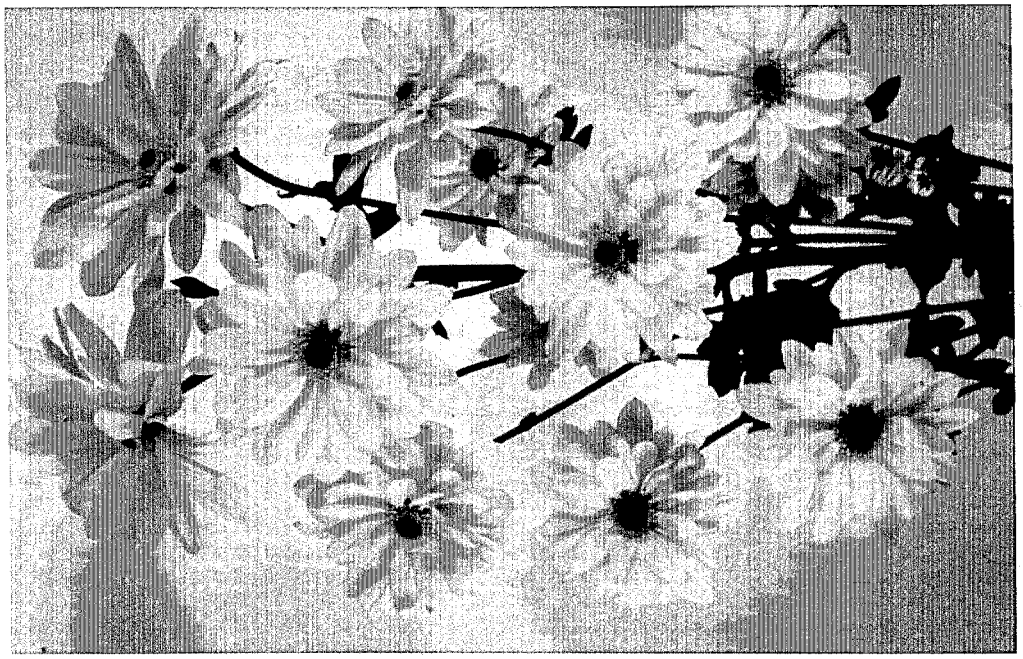

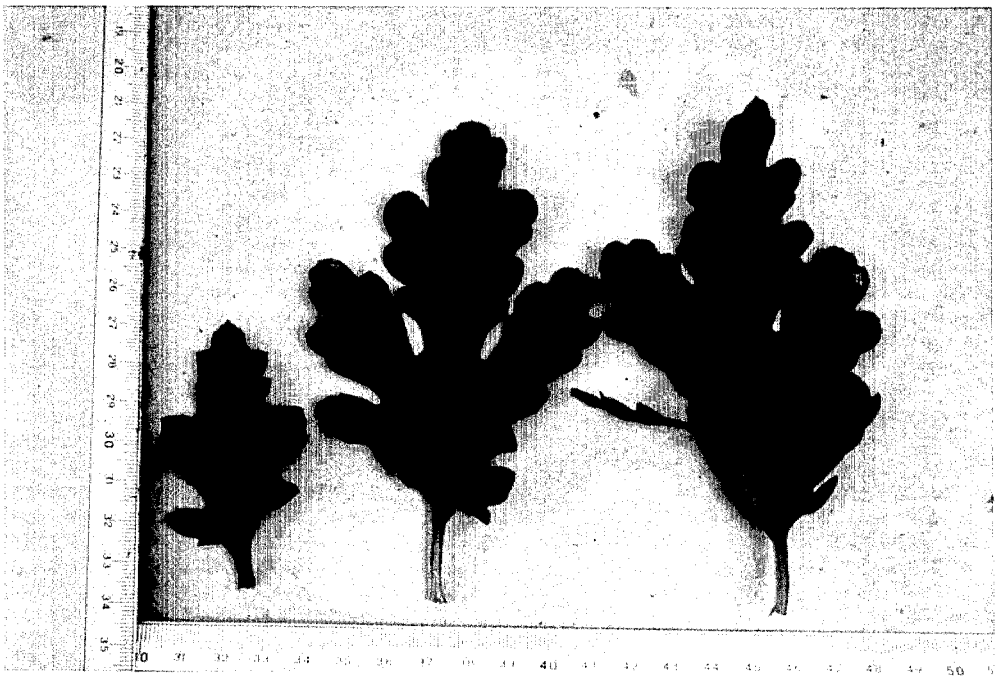
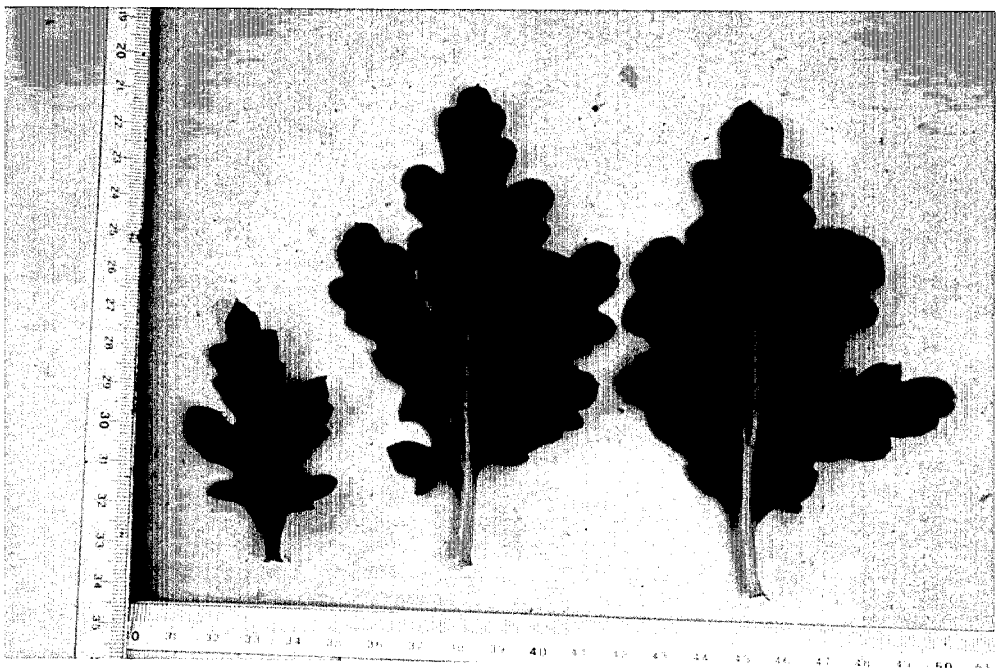

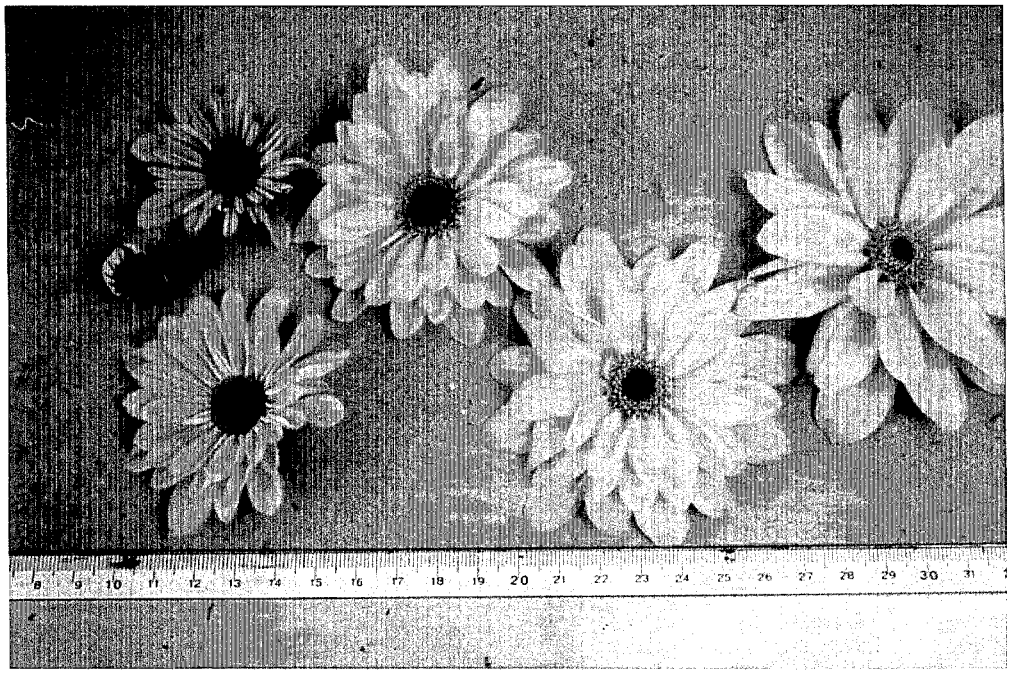
8 9 10 11 12 13 14 15 16 17 18 19 20 21 22 23 24 25 26 27 28 29 30 31